US012390231B2

(12) United States Patent
Perez et al.

(10) Patent No.: US 12,390,231 B2
(45) Date of Patent: Aug. 19, 2025

(54) BONE GRAFT HARVESTER (71) Applicant: In2Bones USA, LLC, Memphis, TN (US)

(72) Inventors: Arley Perez, Memphis, TN (US); Rebecca Hawkins Wahl, Escondido, CA (US)

(73) Assignee: In2Bones USA, LLC, Memphis, TN (US)

( * ) Notice: Subject to any disclaimer, the term of this patent is extended or adjusted under 35 U.S.C. 154(b) by 615 days.

(21) Appl. No.: 17/529,949

(22) Filed: Nov. 18, 2021

(65) Prior Publication Data

US 2022/0071641 A1 Mar. 10, 2022

Related U.S. Application Data (63) Continuation of application No. 16/285,637, filed on Feb. 26, 2019, now Pat. No. 11,185,339.

(51) Int. Cl.
*A61B 17/16* (2006.01)
*A61F 2/28* (2006.01)
*A61F 2/46* (2006.01)
*A61B 17/00* (2006.01)

(52) U.S. Cl.
CPC ............ *A61B 17/1635* (2013.01); *A61F 2/28* (2013.01); *A61F 2/4601* (2013.01); *A61B 2017/00969* (2013.01); *A61F 2002/2835* (2013.01)

(58) Field of Classification Search
CPC .................................................. A61B 17/1635
See application file for complete search history.

(56) References Cited

U.S. PATENT DOCUMENTS

| 14,454 | A | * | 3/1856 | Hitchcock | ............... B23B 51/10 408/207 |
| 1,493,240 | A | * | 5/1924 | Bohn | ................. A61B 17/1688 30/29.5 |
| 1,807,126 | A | * | 5/1931 | Morrill | ................... B27G 15/00 408/59 |
| 5,556,399 | A | * | 9/1996 | Huebner | .............. A61B 10/025 408/207 |
| 5,833,628 | A | * | 11/1998 | Yuan | .................. A61B 17/1664 606/180 |
| 5,873,886 | A | | 2/1999 | Larsen | |
| 5,954,671 | A | | 9/1999 | O'Neill | |
| 2008/0077147 | A1 | * | 3/2008 | Marino | .............. A61B 17/1635 606/80 |
| 2008/0177200 | A1 | | 7/2008 | Ikehara et al. | |

(Continued)

*Primary Examiner* — Nicholas W Woodall
(74) *Attorney, Agent, or Firm* — Rutan & Tucker LLP; Hani Z. Sayed (57) ABSTRACT An apparatus and methods are provided for a trephine bone graft harvester for extracting morselized bone from patients. The trephine bone graft harvester includes a bone cutter affixed to an outer hub. The bone cutter comprises a hollow tube having cylindrical wall and a distal cutting edge. A bone graft collector is sheathed within the bone cutter. The bone graft collector includes a distal scoop adjacent to the distal cutting edge of the bone cutter. The distal scoop is configured to move morselized bone away from the distal cutting edge. An inner hub is affixed to the bone graft collector and coupled with the outer hub. The inner hub includes a proximal shank configured to be engaged with a rotary tool suitable for applying torque to the inner hub.

11 Claims, 4 Drawing Sheets (56) References Cited

U.S. PATENT DOCUMENTS

| | | |
|---|---|---|
| 2009/0326486 A1 | 12/2009 | Miller et al. |
| 2013/0317507 A1* | 11/2013 | Khanna .............. A61B 17/1635 606/80 |
| 2015/0045799 A1 | 2/2015 | Budyansky et al. |
| 2016/0302777 A1 | 10/2016 | Marino et al. |
| 2017/0340455 A1 | 11/2017 | Greter |
| 2018/0014707 A1 | 1/2018 | Budyansky |
| 2020/0060696 A1* | 2/2020 | Zastrow ............. A61B 17/1633 |

* cited by examiner

BONE GRAFT HARVESTER

PRIORITY

This application claims the benefit of and priority to U.S. patent application Ser. No. 16/285,637 filed Feb. 26, 2019 and U.S. Provisional application, entitled "Bone Graft Harvester," filed on Jun. 22, 2018 and having application Ser. No. 62/688,980, the entirety of said application being incorporated herein by reference.

FIELD

Embodiments of the present disclosure generally relate to the field of extracting bone grafts. More specifically, embodiments of the disclosure relate to devices and methods for harvesting morselized bone from a patient.

BACKGROUND

Grafting generally is a surgical procedure whereby a portion of living tissue is transplanted from one location on a patient to another operative location on the patent so as to assist with healing following surgery. For example, bone grafting is very common in orthopedic surgery, neuro/spine surgery, and plastic surgery. As will be appreciated, bone generally has an ability to regenerate completely; but in many cases, some sort of scaffold is required to encourage bone adhesion and growth.

In practice, bone grafts may be autograft (bone harvested from the patient's own body, often from the iliac crest), allograft (cadaveric bone usually obtained from a bone bank), as well as synthetic (often made of hydroxyapatite or other naturally occurring and biocompatible substances) with similar mechanical properties to bone. Most bone grafts are expected to be reabsorbed and replaced as the natural bone heals over time.

Autografts are desirable because they are essentially guaranteed to be biocompatible, osteoconductive, osteoinductive, and osteogenic. A drawback to harvesting autograft bone, however, is that it requires harvesting the bone from a separate donor site, thereby requiring additional surgery. Many patients complain that the pain associated with the donor site is greater than the pain associated with the primary operative site. As such, there is a continuing desire to develop bone harvesting capabilities that limit donor site pain, speed the harvesting process, and provide adequate bone volume for a variety of surgical needs.

SUMMARY

An apparatus and methods are provided for a trephine bone graft harvester for extracting morselized bone from a patient. The trephine bone graft harvester comprises a bone graft collector that is sheathed within a bone cutter. The bone cutter includes a distal cutting edge and a proximal handle. The distal cutting edge includes sharpened edges configured to morselize bone during rotation of the bone cutter. A distal scoop comprising the bone graft collector is configured to move the morselized bone away from the distal cutting edge during extracting bone from an autograft site. The proximal handle includes an outer hub configured to engage with an inner hub comprising the bone graft collector. A proximal shank comprising the bone graft collector is configured to engage with a rotary tool suitable for applying torque to the inner hub. The inner hub and the outer hub are configured to cooperatively convey torque from the rotary tool to the bone graft collector and the bone cutter.

In an exemplary embodiment, a trephine bone graft harvester for extracting bone from an autograft site comprises: a bone cutter that includes a distal cutting edge and a proximal handle; a bone graft collector that is sheathed within the bone cutter; and a proximal shank comprising the bone graft collector configured to engage with a rotary tool.

In another exemplary embodiment, the proximal handle includes an outer hub configured to engage with an inner hub comprising the bone graft collector. In another exemplary embodiment, the outer hub and the inner hub are configured to enable removal of the bone graft collector from an interior of the bone cutter. In another exemplary embodiment, the bone graph collector includes pins disposed on opposite sides of the inner hub and configured to be received into slots disposed on opposite sides of the outer hub. In another exemplary embodiment, the pins and the slots are respectively positioned on the bone graft collector and the bone cutter such that a distal scoop comprising the bone graft collector is optimally positioned with respect to the distal cutting edge when the bone graft collector is sheathed within the bone cutter.

In another exemplary embodiment, the pins are configured to be retained within the slots by way of snap lock portions comprising levers disposed on opposite sides of the proximal handle. In another exemplary embodiment, the snap lock portions are biased toward the outer hub by flexible portions that attach the levers to a body comprising the proximal handle. In another exemplary embodiment, the flexible portions are configured to allow the snap lock portions to pivot the levers slightly as the pins are pushed into the slots during insertion of the bone graft collector into the bone cutter. In another exemplary embodiment, the snap lock portions are configured to allow the pins to be removed from the slots upon a practitioner squeezing the levers together.

In another exemplary embodiment, the bone cutter comprises a cylindrical wall that is joined with a body comprising the proximal handle. In another exemplary embodiment, the distal cutting edge comprises an angled wedge portion of the cylindrical wall and includes sharpened edges configured to morselize bone during rotation of the bone cutter. In another exemplary embodiment, the body is configured to be grasped in a hand. In another exemplary embodiment, the body includes substantially similar levers disposed on opposite sides of the body that are configured to engage with and retain an inner hub of the bone graft collector.

In another exemplary embodiment, the bone graft collector comprises a hollow tube having an open-tube portion that includes a distal scoop. In another exemplary embodiment, the open-tube portion is joined with the proximal shank by way of the inner hub. In another exemplary embodiment, the bone graft collector is configured to position the distal scoop adjacent to the distal cutting edge when the bone graft collector is sheathed within the bone cutter. In another exemplary embodiment, the distal scoop is configured to move morselized bone away from the distal cutting edge during extracting bone from the autograft site. In another exemplary embodiment, the bone graft collector is configured to retain morselized bone within the open-tube portion until retrieval by a practitioner.

In an exemplary embodiment, a trephine bone graft harvester comprises: a bone cutter including a distal cutting edge; an outer hub affixed to a proximal end of the bone cutter; a bone graft collector disposed within the bone cutter; and an inner hub affixed to the bone graft collector and coupled with the outer hub.

In another exemplary embodiment, the bone cutter comprises a tube-shaped member having an interior that slidably receives the bone graft collector. In another exemplary embodiment, the inner hub is configured to allow removal of the bone graft collector from the interior of the bone cutter, such that morselized bone may be retrieved from the bone graft collector. In another exemplary embodiment, the bone graft collector includes a distal scoop configured to retain morselized bone within an interior of the bone cutter. In another exemplary embodiment, the distal scoop facilitates retrieval of the morselized bone after removal of the bone graft collector from within the bone cutter.

In another exemplary embodiment, the inner hub includes a proximal shank that is configured to be engaged with a rotary tool suitable for applying torque to the inner hub. In another exemplary embodiment, the inner hub and the outer hub are configured to cooperatively convey torque from the rotary tool to the bone graft collector and the bone cutter. In another exemplary embodiment, the distal cutting edge is configured to morselize bone during rotation of the bone cutter.

In an exemplary embodiment, a method for a trephine bone graft harvester comprises: configuring a distal cutting edge of a bone cutter; affixing an outer hub to a proximal end of the bone cutter; disposing a bone graft collector within an interior of the bone cutter; affixing an inner hub to the bone graft collector; and coupling the inner hub to the outer hub.

In another exemplary embodiment, a coupling includes causing the bone graft collector and the bone cutter rotate together upon applying torque to a proximal shank comprising the inner hub. In another exemplary embodiment, disposing the bone graft collector includes forming a distal scoop to retain morselized bone within an interior of the bone cutter. In another exemplary embodiment, configuring a distal cutting edge includes forming an angled wedge portion of the bone cutter to morselize bone upon rotating the bone cutter.

In an exemplary embodiment, trephine bone graft harvester comprises: a bone cutter affixed to an outer hub; a bone graft collector sheathed within the bone cutter; and an inner hub affixed to the bone graft collector and coupled with the outer hub.

In another exemplary embodiment, the bone cutter comprises a hollow tube having cylindrical wall and a distal cutting edge. In another exemplary embodiment, the distal cutting edge comprises an angled wedge portion of the cylindrical wall having sharpened edges and configured to morselize bone during rotation of the bone cutter. In another exemplary embodiment, the bone graft collector includes a distal scoop adjacent to the distal cutting edge and is configured to migrate morselized bone into an interior of the bone graft collector. In another exemplary embodiment, the distal scoop retains the morselized bone within the interior during removal of the bone graft collector from the bone cutter.

In another exemplary embodiment, the inner hub includes a proximal shank that is configured to be engaged with a rotary tool suitable for applying torque to the inner hub. In another exemplary embodiment, the inner hub is configured to rotate the bone graft collector and the bone cutter, the inner hub being coupled with the bone cutter by way of the outer hub. In another exemplary embodiment, the bone cutter is configured to morselize bone during rotation of the bone cutter. In another exemplary embodiment, the inner hub includes a fastener and a key whereby the inner hub may be removably coupled with the outer hub, the key being configured to convey torque from the inner hub to the outer hub. In another exemplary embodiment, the proximal shank is configured to be received by a chuck comprising the rotary tool.

In another exemplary embodiment, the bone graft collector includes a distal scoop configured to be disposed adjacent to a distal cutting edge of the bone cutter, the distal scoop being configured to move morselized bone away from the distal cutting edge. In another exemplary embodiment, the distal scoop is configured to retain the morselized bone within the bone graft collector, such that the morselized bone may be retrieved upon removing the bone graft collector from an interior of the bone cutter. In another exemplary embodiment, the bone graft collector includes a half-tube portion adjacent to the distal scoop, the half-tube portion being configured to facilitate removal of the morselized bone upon removal of the bone graft collector from an interior of the bone cutter.

BRIEF DESCRIPTION OF THE DRAWINGS

The drawings refer to embodiments of the present disclosure in which.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first bone graft," may be made. However, the specific numeric reference should not be interpreted as a literal sequential order but rather interpreted that the "first bone graft" is different than a "second bone graft." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

In general, the present disclosure describes an apparatus and methods for a trephine bone graft harvester for extracting morselized bone from patients. The trephine bone graft harvester includes a bone graft collector sheathed within a bone cutter. The bone cutter comprises a hollow tube having a distal cutting edge and a proximal outer hub. The bone graft collector includes a distal scoop adjacent to the distal cutting edge of the bone cutter and an inner hub that engages with the outer hub of the bone cutter. The distal scoop is configured to move morselized bone away from the distal cutting edge. The inner hub includes a proximal shank configured to be engaged with a rotary tool suitable for applying torque to the inner hub.

Figure 1:
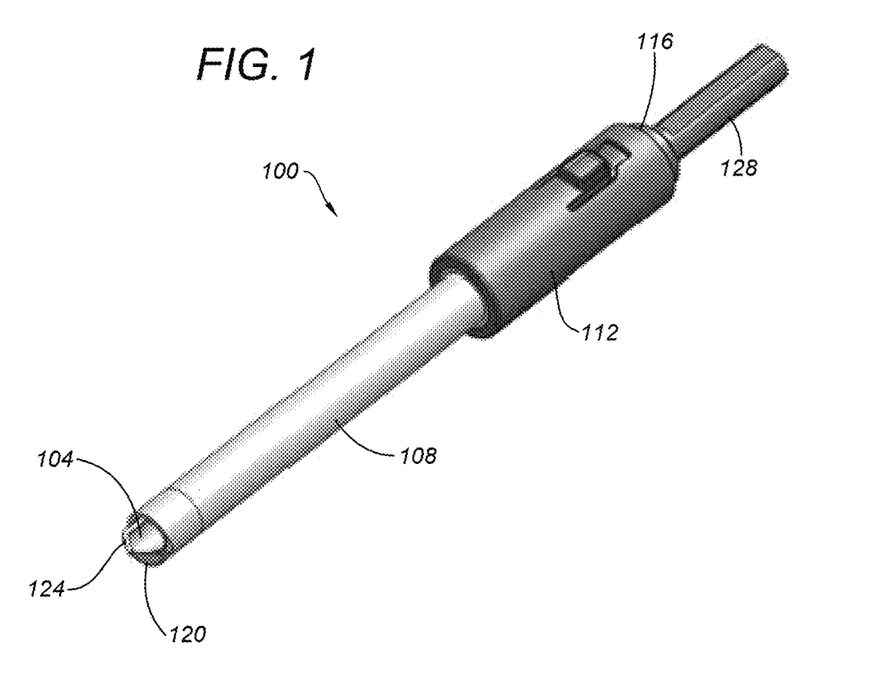
FIG. 1 illustrates an isometric view of an exemplary embodiment of a trephine bone graft harvester, according to the present disclosure.
Figure 2:
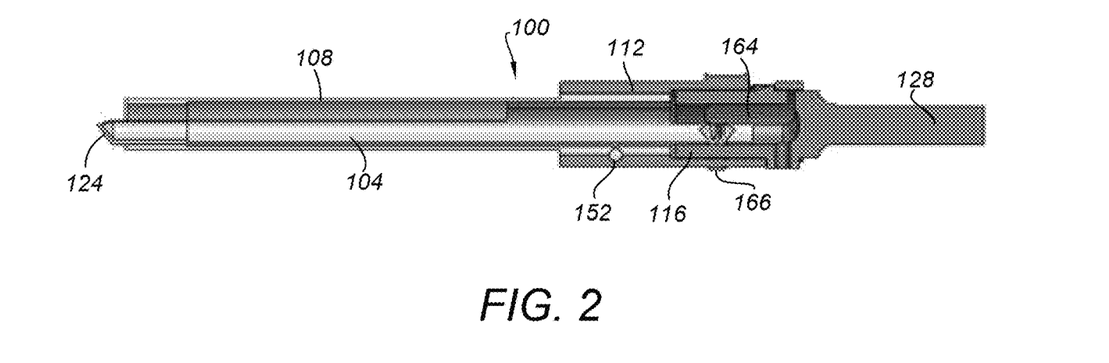
FIG. 2 illustrates a cross-sectional view of the trephine bone graft harvester of FIG. 1, taken along a line 2-2.

FIG. 1 illustrates an exemplary embodiment of a trephine bone graft harvester 100, according to the present disclosure. The harvester 100 is a generally elongate assembly that includes a bone graft collector 104 that is sheathed within a bone cutter 108, as best shown in FIG. 2. In the illustrated embodiment of FIG. 1, the bone cutter 108 is affixed to an outer hub 112, while the bone graft collector 104 is affixed to an inner hub 116. As described herein, the outer hub 112 is engaged with the inner hub 116, such that disengaging of the outer and inner hubs 112, 116 enables a practitioner to remove the bone graft collector 104 from an interior of the bone cutter 108. The harvester 100 includes a distal cutting edge 120 and a distal scoop 124, as well as a proximal shank 128 that may be engaged with a suitable rotary tool capable of rotating the harvester 100 for the purpose of extracting bone from an autograft site.

Figure 3:
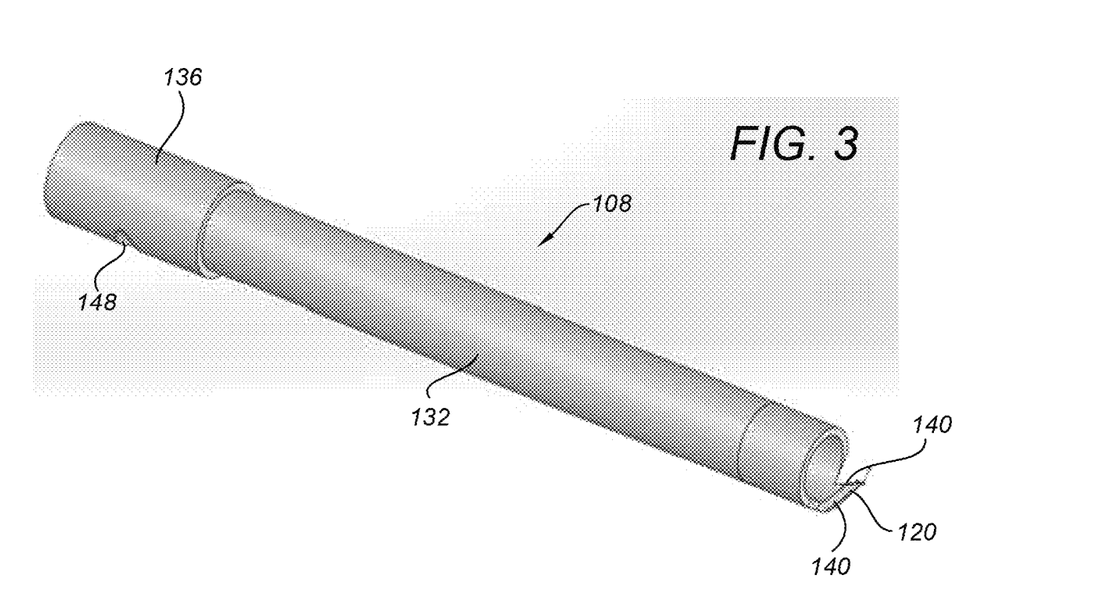
FIG. 3 illustrates an isometric view of an exemplary embodiment of a bone cutter comprising a trephine bone graft harvester, according to the present disclosure.

FIG. 3 illustrates an exemplary embodiment of the bone cutter 108 comprising the trephine bone graft harvester 100, according to the present disclosure. The bone cutter 108 comprises a generally hollow tube having a cylindrical wall 132 that includes a proximal portion 136 and the distal cutting edge 120. The distal cutting edge 120 comprises an angled wedge portion of the cylindrical wall 132 and includes sharpened edges 140 that are configured to morselize bone during rotation of the bone cutter 108. The proximal portion 136 comprises a relatively thicker portion of the cylindrical wall 132 and is configured to be affixedly received into a distal opening 144 (see FIG. 5) of the outer hub 112, as discussed herein. The proximal portion 136 includes a keyed opening 148 that facilitates mechanically affixing the bone cutter 108 to the outer hub 112, such as by way of a key 152 as shown in FIG. 2.

Figure 4:
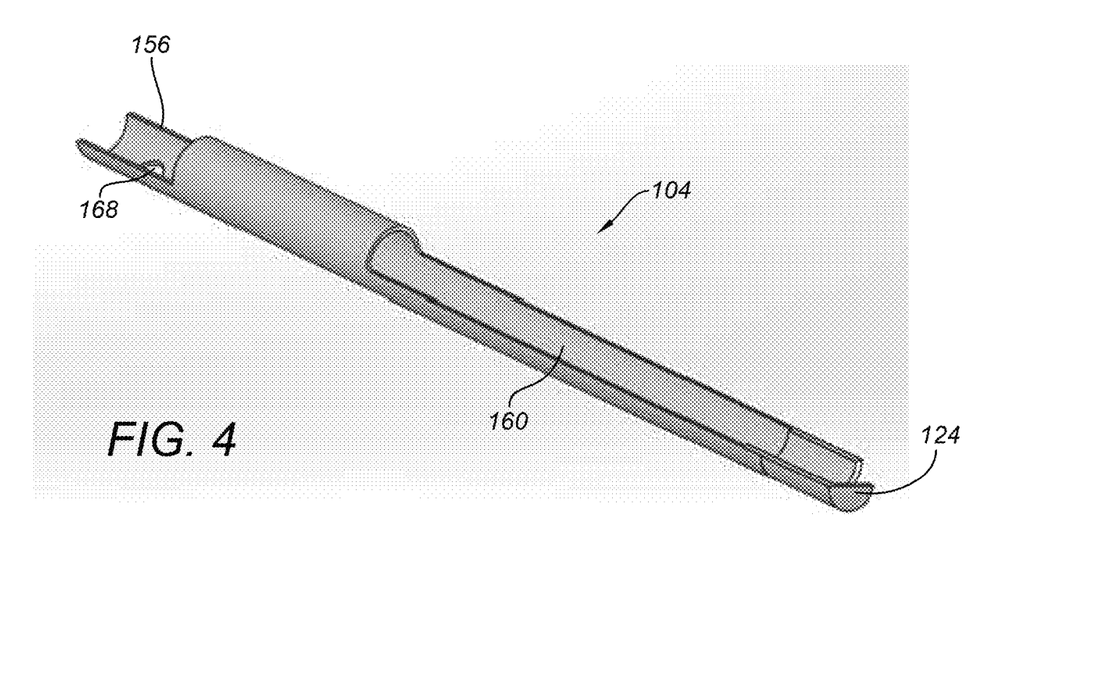
FIG. 4 illustrates an isometric view of an exemplary embodiment of a bone graft collector comprising a trephine bone graft harvester in accordance with the present disclosure.

FIG. 4 illustrates an exemplary embodiment of the bone graft collector 104 comprising the trephine bone graft harvester 100 in accordance with the present disclosure. The bone graft collector 104 comprises a generally hollow tube having a proximal portion 156 and an open-tube portion 160 that includes the distal scoop 124. The proximal portion 156 is configured to be affixed within a central opening 164 disposed in the inner hub 116, as shown in FIG. 2. In the embodiment illustrated in FIG. 4, the proximal portion 156 includes a keyed opening 168 that is configured to receive a lock pin 166 comprising the inner hub 116, as shown in FIG. 2. As will be appreciated, inserting the lock pin 166 into the keyed opening 168 affixes the bone graft collector 104 and the inner hub 116.

With continuing reference to FIG. 4, the bone graft collector 104 is configured to position the distal scoop 124 adjacent to the distal cutting edge 120. The distal scoop 124 is configured to move morselized bone away from the distal cutting edge 120 during extracting bone from a patient. Further, the distal scoop 124 is configured to retain the morselized bone within the bone graft collector 104, such that the morselized bone may be retrieved upon removing the bone graft collector 104 from the interior of the bone cutter 108. In the embodiment illustrated in FIG. 4, the open-tube portion 160 adjacent to the distal scoop 124 facilitates retrieving the morselized bone upon removal of the bone graft collector 104 from the interior of the bone cutter 108.

Figure 5:
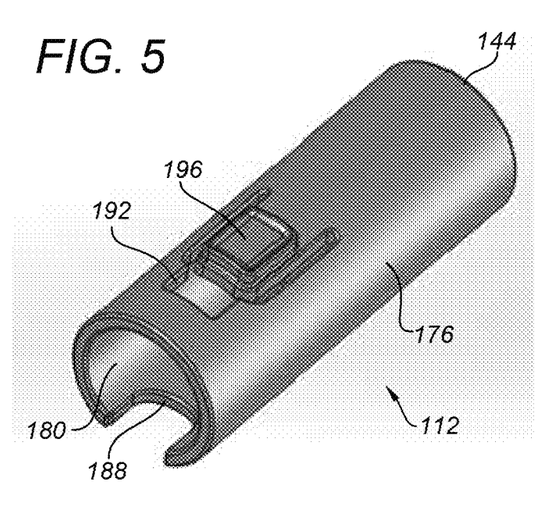
FIG. 5 illustrates an isometric view of an exemplary embodiment of an outer hub comprising a trephine bone graft harvester in accordance with the present disclosure.
Figure 6:
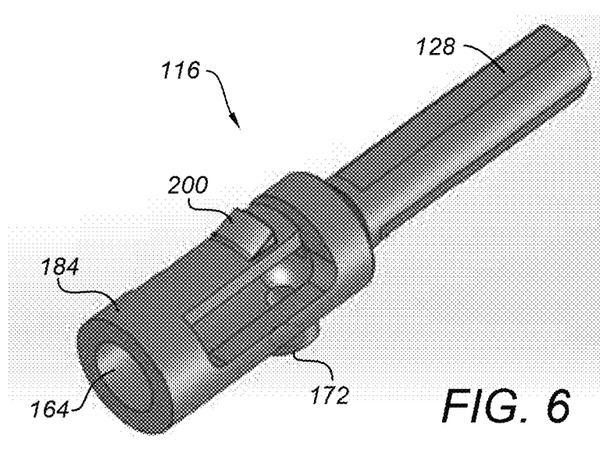
FIG. 6 illustrates an isometric view of an exemplary embodiment of an inner hub comprising a trephine bone graft harvester, according to the present disclosure.

FIGS. 5-6 respectively illustrate exemplary embodiments of the outer hub 112 and the inner hub 116 comprising the trephine bone graft harvester 100 in accordance with the present disclosure. The outer hub 112 comprises a cylindrical member 176 that includes a proximal opening 180 and the distal opening 144. As mentioned above, the distal opening 144 is configured to receive the proximal portion 136 of the bone cutter 108. Although not shown in FIG. 5, the distal opening 144 preferably includes a key that is received by the keyed opening 148 (see FIG. 3) so as to mechanically fixate the bone cutter 108 to the outer hub 112.

With continuing reference to FIGS. 5-6, the proximal opening 180 is configured to slidably receive a distal portion 184 of the inner hub 116. The proximal opening 180 includes a keyed opening 188 that receives a keyed portion 172 of the inner hub 116. The outer hub 112 includes an opening 192 and an actuator 196 disposed in the side of the cylindrical member 176. The opening 192 is configured to receive a flexible protrusion 200 disposed on the inner hub 116 whereby the outer hub 112 and the inner hub 116 may be removably locked together. The actuator 196 is configured to enable a practitioner to remove the flexible protrusion 200 from the opening 192, thereby allowing the practitioner to disengage the outer and inner hubs 112, 116.

As will be appreciated, engaging the keyed portion 172 within the keyed opening 188 effectively fixates the outer hub 112 to the inner hub 116, such that torque applied to the proximal shank 128 is conveyed to both the outer hub 112 and the inner hub 116. In some embodiments, the proximal shank 128 is configured to be received by a chuck comprising a suitable rotary tool. As such, the rotary tool may be engagedly coupled with the proximal shank 128 to rotate both the bone cutter 108 and the bone graft collector 104 for the purpose of extracting bone from a patient. Once a desired quantity of morselized bone has been extracted, the actuator 196 may be used to disengage the outer and inner hubs 112, 116 and allow the bone graft collector 104 to be removed from the interior of the bone cutter 108. As described hereinabove, removal of the bone graft collector 104 from the bone cutter 108 reveals the open-tube portion 160 and allows for retrieval of the extracted quantity of morselized bone.

Figure 7:
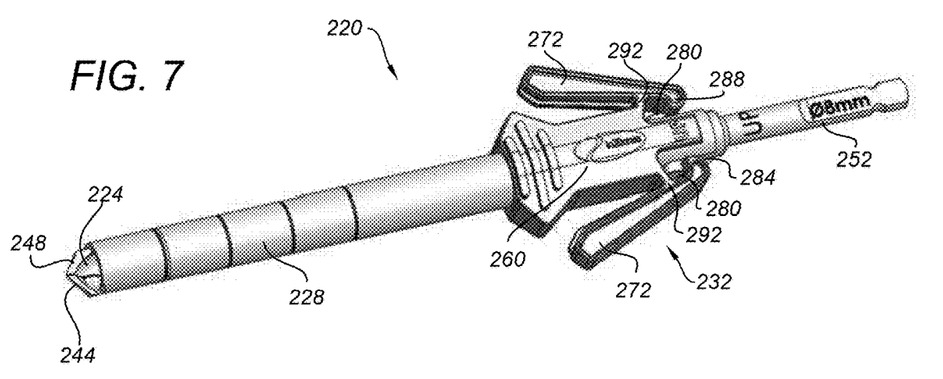
FIG. 7 illustrates an exemplary embodiment of a trephine bone graft harvester in a bone drilling configuration, according to the present disclosure.
Figure 8:
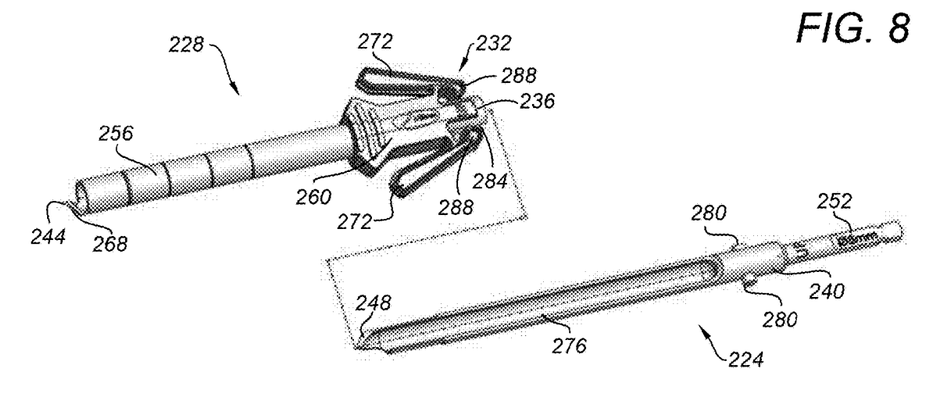
FIG. 8 illustrates an exploded view of the trephine bone graft harvester of FIG. 7 in a graft collection configuration according to the present disclosure.

FIGS. 7-8 illustrate an exemplary embodiment of a trephine bone graft harvester 220, according to the present disclosure. The harvester 220 is a generally elongate assembly that includes a bone graft collector 224 that is sheathed within a bone cutter 228, as best shown in FIG. 8. The bone cutter 228 includes a proximal handle 232 configured to facilitate a practitioner grasping the harvester 200 during extracting bone. The handle 232 includes an outer hub 236 that engages with an inner hub 240 comprising the bone graft collector 224. As described herein, disengaging the outer and inner hubs 236, 240 enables the practitioner to remove the bone graft collector 224 from an interior of the bone cutter 228. The harvester 200 includes a distal cutting edge 244 and a distal scoop 248, as well as a proximal shank 252 that may be engaged with a suitable rotary tool capable of rotating the harvester 200 for the purpose of extracting bone from an autograft site.

As best shown in FIG. 8, the bone cutter 228 comprises a generally hollow tube having a cylindrical wall 256 that is joined with a proximal body 260. The cylindrical wall 256 includes a distal cutting edge 264 that comprises an angled wedge portion of the cylindrical wall 256 and includes sharpened edges 268 configured to morselize bone during rotation of the bone cutter 228. The body 260 generally comprises a portion of the handle 232 that is configured to be grasped in a hand of the practitioner during operation of the harvester 200. As described herein, the body 260 includes substantially similar levers 272 disposed on opposite sides of the body 260 that are configured to engage with the inner hub 240 of the bone graft collector 224.

With continuing reference to FIG. 8, the bone graft collector 224 comprises a generally hollow tube having an open-tube portion 276 that includes the distal scoop 248. The open-tube portion 276 is joined with the proximal shank 252 by way of the inner hub 240. The bone graft collector 224 is configured to position the distal scoop 248 adjacent to the distal cutting edge 244 when the bone graft collector 224 is sheathed within the bone cutter 228. The distal scoop 248 is configured to move morselized bone away from the distal cutting edge 244 during extracting bone from a patient, as well as retain the morselized bone within the bone graft collector 104 until retrieval by the practitioner. As will be appreciated, the morselized bone may be retrieved upon removing the bone graft collector 224 from the interior of the bone cutter 228 to expose the morselized bone within the open-tube portion 276 adjacent to the distal scoop 248.

As shown in FIG. 8, the bone graph collector 224 includes pins 280 that are disposed on opposite sides of the inner hub 240. The pins 280 are configured to be received into slots 284 disposed on opposite sides of the outer hub 236 of the bone cutter 228. The pins 280 and the slots 284 are respectively positioned on the bone graft collector 224 and the bone cutter 228 such that the distal scoop 248 is optimally positioned with respect to the distal cutting edge 244 when the bone graft collector 224 is sheathed within the bone cutter 228 as shown in FIG. 7. The pins 280 are configured to be retained within the slots 284 by way of a snap lock portion 288 comprising each of the levers 272, as shown in FIG. 7. The snap lock portions 288 are biased toward the outer hub 236 by flexible portions 292 that attach the levers 272 to the body 260. The flexible portions 292 allow the snap lock portions 288 to pivot the levers 272 slightly as the pins 280 are pushed into the slots 284 during insertion of the bone graft collector 224 into the bone cutter 228. As will be recognized, the snap lock portions 288 allow the pins 280 to be removed from the slots 284 upon the practitioner squeezing the levers 272 together.

Methods for a trephine bone graft harvester 100 include, in some embodiments, configuring a distal cutting edge 120 of a bone cutter 108, affixing an outer hub 112 to a proximal end of the bone cutter 108, disposing a bone graft collector 104 within an interior of the bone cutter 108, affixing an inner hub 116 to the bone graft collector 104, and coupling the inner hub 116 to the outer hub 112.

In some embodiments, methods for a trephine bone graft harvester 100 include coupling an inner hub 116 to an outer hub 112. In some embodiments, coupling the inner hub 116 to the outer hub 112 further includes causing the bone graft collector 104 and the bone cutter 104 to rotate together upon applying torque to a proximal shank 128 comprising the inner hub 116.

In some embodiments, methods for a trephine bone graft harvester 100 include disposing a bone graft collector 104 within an interior of the bone cutter 108. The methods may further include, in some embodiments, forming a distal scoop 124 to retain morselized bone within an interior of the bone cutter 108.

In some embodiments, methods for a trephine bone graft harvester 100 include configuring a distal cutting edge 120 of a bone cutter 108. Further, in some embodiments, the methods for configuring the distal cutting edge 120 may include forming an angled wedge portion of the bone cutter 108 having sharpened edges 140 to morselize bone upon rotating the bone cutter 108.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A trephine bone graft harvester, comprising:
  a bone cutter for morselizing bone wherein the bone cutter comprises a hollow tube having a cylindrical wall;
  the bone cutter includes a proximal portion configured to be received into the outer hub wherein the proximal portion includes an opening configured to receive a key comprising the outer hub;
  a bone graph collector for retaining the morselized bone;
  a proximal shank for engaging with a rotary tool;
  an outer hub coupled with the bone cutter; and
  an inner hub coupled with the bone graph collector.

2. The bone graft harvester of claim 1, wherein the outer hub engages with the inner hub such that the bone graph collector is sheathed within the bone cutter.

3. The bone graft harvester of claim 1, wherein the outer hub and the inner hub are disengageable to enable removal of the bone graft collector from an interior of the bone cutter.

4. The bone graft harvester of claim 1, wherein the bone cutter includes a distal cutting edge configured for morselizing bone during rotation of the bone cutter.

5. The bone graft harvester of claim 4, wherein the distal cutting edge comprises an angled wedge portion of the cylindrical wall that includes sharpened edges.

6. The bone graft harvester of claim 1, wherein the bone graft collector comprises a hollow tube configured to be sheathed within the bone cutter.

7. The bone graft harvester of claim 6, wherein the bone graft collector includes a distal scoop configured to receive the morselized bone from the bone cutter.

8. The bone graft harvester of claim 7, wherein the distal scoop is configured to move the morselized bone into the bone graft collector.

9. The bone graft harvester of claim 8, wherein the distal scoop is configured to retain the morselized bone within the bone graft collector during removal of the bone graft collector from the bone cutter.

10. The bone graft harvester of claim 6, wherein the bone graph collector includes a proximal portion configured to engage within a central opening of the inner hub.

11. The bone graft harvester of claim 10, wherein the proximal portion includes a keyed opening for receiving a lock pin comprising the inner hub.

* * * * *